(12) United States Patent
Dong et al.

(10) Patent No.: US 7,008,430 B2
(45) Date of Patent: Mar. 7, 2006

(54) ADJUSTABLE REAMER WITH TIP TRACKER LINKAGE

(75) Inventors: Nicholas N. Dong, Little Falls, NJ (US); Michael Nogler, Oberperfuss (AT); Martin Krismer, Grinzens (AT)

(73) Assignee: Howmedica Osteonics Corp., Mahwah, NJ (US)

( * ) Notice: Subject to any disclaimer, the term of this patent is extended or adjusted under 35 U.S.C. 154(b) by 431 days.

(21) Appl. No.: 10/356,075

(22) Filed: Jan. 31, 2003

(65) Prior Publication Data

US 2004/0153080 A1 Aug. 5, 2004

(51) Int. Cl.
*A61B 17/00* (2006.01)

(52) U.S. Cl. ........................................ 606/80

(58) Field of Classification Search .................. 606/53, 606/79, 80, 81, 86, 91, 87, 96, 97, 98, 99, 606/104
See application file for complete search history.

(56) References Cited

U.S. PATENT DOCUMENTS

| | | | |
|---|---|---|---|
| 3,702,611 A | 11/1972 | Fishbein | |
| 4,305,394 A | 12/1981 | Bertuch, Jr. | |
| 4,632,111 A | 12/1986 | Roche | |
| 5,037,424 A | 8/1991 | Aboczsky | |
| 5,061,270 A | 10/1991 | Aboczky | |
| 5,320,625 A | 6/1994 | Bertin | |
| 5,383,454 A | 1/1995 | Bucholz | |
| 5,397,323 A * | 3/1995 | Taylor et al. | ................ 606/130 |

(Continued)

FOREIGN PATENT DOCUMENTS

DE 199 64 009 A1 7/2001

(Continued)

*Primary Examiner*—Eduardo C. Robert
*Assistant Examiner*—Anu Ramana
(74) *Attorney, Agent, or Firm*—Lerner, David, Littenberg, Krumholz & Mentlik, LLP

(57) ABSTRACT

A positioning tool for a joint socket cutting instrument or a implant is designed for use with a minimally invasive surgical procedure and in conjunction with a computer assisted surgical procedure. The positioning tool has a longitudinally extending drive shaft having a moveable joint at a first end and a drive coupling for connecting to a power source at a second end. A holder for mounting a cutting tool such a drill or as an acetabular cutting instrument or for mounting an acetabular implant is coupled to the moveable joint at the first end of the drive shaft for movement with respect to the drive shaft. The holder is rotatable about a central axis thereof when the drive shaft is rotated. The drive shaft includes a shaft bearing mounted thereon which is pivotally coupled to the shaft at a fixed longitudinal position and is pivotally coupled to a longitudinally extending first arm having a handle. A tracker system which is capable of being utilized by a computer-aided surgical system is mounted on the first arm. A second arm is provided which is pivotally connected to the holder at a first end and pivotally connected to the first arm at a second end. The resulting four bar linkage allows the holder and the cutting instrument/implant to be manipulated in any position while the known geometric relationship between the tracker and the holder allows the location of the holder to be displayed by the computer on a cathode ray tube with respect to a joint.

26 Claims, 8 Drawing Sheets

U.S. PATENT DOCUMENTS

| | | |
|---|---|---|
| 5,925,077 A | 7/1999 | Blasche et al. |
| 6,021,343 A | 2/2000 | Foley et al. |
| 6,264,647 B1 | 4/2002 | Lechot |
| 6,377,011 B1 * | 4/2002 | Ben-Ur .................. 318/566 |
| 6,385,475 B1 | 5/2002 | Cinquin et al. |
| 6,395,005 B1 | 5/2002 | Lovell |
| 6,406,472 B1 * | 6/2002 | Jensen ........................ 606/1 |
| 6,434,415 B1 | 8/2002 | Foley et al. |

FOREIGN PATENT DOCUMENTS

FR    2 721 502 A1    12/1995

* cited by examiner

ADJUSTABLE REAMER WITH TIP TRACKER LINKAGE

BACKGROUND OF THE INVENTION

The present invention is directed to the implantation of artificial joint components and in particular to acetabular joint components. More particularly, it is related to instrumentation for reaming the acetabular socket and for locating the prosthetic acetabular cup within the reamed socket. Even more particularly, it is related to an instrument which can be used with computer-assisted minimally invasive surgical implantation of the joint component during joint replacement or revision procedures.

Total hip replacement or orthroplasty operations have been performed to repair the acetabulum and the regions surrounding it and to replace the hip components such as the natural femoral head which has degenerated.

With regard to the acetabulum, many instruments have been designed to locate either the acetabular cup or reamers for repairing the acetabulum to receive such a prosthetic cup. Such instruments are shown in U.S. Pat. Nos. 4,305,394, 4,632,111, 5,037,424, 5,061,270, 5,320,625 and 6,395,005. Many of these instruments require a relatively large incision, i.e., 7–9 inches in the hip area in order to utilize the instruments in preparing the acetabulum and positioning the acetabular cup. There has been a long felt need to develop instrumentation to perform this procedure which can be used with a smaller incision, for example, 2–3 inches.

In addition, computer-assisted surgery has been developed which utilizes a tracking system which can relate positions on the patients and/or instruments to stored X-ray, CT scan and MRI data previously obtained for the patient. Alternately, image free computer-aided surgery has been developed where mechanical relationships can be calculated from anatomical reference points and utilized such as in joint arthroplasty. Such digitized points include the location of the center of the femoral head, the location of the epicondylar ligament attachment points, and the surfaces of the condyles. These systems are used intra-operatively for performing various surgical procedures, including replacement of artificial joints.

It has been especially useful to utilize trackable medical instruments for use in procedures utilizing computer-assisted image guided or image free medical and surgical navigation systems. Systems using body images are shown in U.S. Pat. No. 5,383,454 to Bucholz and U.S. Pat. No. 6,021,343 to Foley et al. In general, these image-guided systems use computer stored digital images of a body part obtained, such as by CT scans taken before surgery, to generate images on a display, such as a CRT monitor screen, during surgery. These images are used in connection with real time information for representing the position of a surgical instrument with respect to the body part. The systems typically include tracking devices such as, for example, an LED array mounted on a surgical instrument as well as a patient body part or parts. A tracker such as an optical tracker is used to track, in real time, the position of the body part and the instrument used during surgery, and a monitor screen to display images representing the body and the position of the instrument relative to the stored images or a vertical image as the surgical procedure is performed.

An image free type system is shown in U.S. Pat. No. 6,385,475 the teachings of which are incorporated herein by reference. Some systems of this type include virtual joint images and relate the tracked anatomic landmarks to the virtual body part images. In such a system, an active or passive marker is attached to bones on opposite sides of a joint and a measuring device such as an optical sensing camera is coupled to a data processing system to which signals corresponding to the positioning data of the optical markers are supplied by the optical camera system. This data is used to correlate the markers on opposite sides of the joint with digitized anatomic landmarks. With a pointer mounted tracker, it is possible to locate various anatomic reference points on the joints to allow the optical/computer system to position a cutting instrument such as a reamer or sawblade having a tracker mounted thereon to shape a joint part for receiving a prosthetic implant.

In utilizing instruments which rotate such as reaming systems, it is important to align the cutting tool in the correct angle as well as locating and controlling the depth of penetration. There has been a long felt need for a tool which can axially align a reamer such as an acetabular reamer and guide the reamer internally of the body to a precise desired location. In addition, in order to perform minimally invasive surgery, reamers have been designed for the acetabulum which, rather than having the standard hemispherical shape, have only a part hemispherical shape but must be rotated through an angle such as 180° to form the hemispherical surface of an acetabular cavity in the pelvis designed to receive a hemispherical prosthetic acetabular component. An expandable reamer such as shown in U.S. Pat. No. 3,702,611 may be used.

SUMMARY OF THE INVENTION

It is an object of the invention to provide an instrument on which a reamer or implant is held which can be manipulated within the body to align the reamer or implant in a desired position.

It is a further object of the invention to provide a holder which can be used with a joint shaper such as an acetabular reamer and/or to position an implant such as an acetabular cup within the body at any angle with respect to the central axis of the cup or reamer.

It is still an additional object of the invention to provide an instrument for positioning a cutting tool or implant on which instrument a tracker, such as an optical tracker, for example, an emitter array, such as a light emitting diode array. The array includes a plurality of light emitters. The tracker can be mounted on an instrument and can interact with an optical tracking system to track the position of the cutting tool, such as a reamer, or an implant, including its axial orientation with respect to a bony target while the instrument is located within the body of a patient.

These and other objects of the invention are achieved by a positioning tool for use in a socket joint such as an acetabular cutting instrument or acetabular implant which tool has a longitudinally extending shaft extending along a longitudinal axis which shaft has a joint capable of movement about at least two axis and preferably three axis at a first end thereof. An implant or tool holder is mounted on the first end of the shaft and is designed to be placed within the body adjacent a socket joint such as the acetabulum. The holder has a central axis and is coupled at a connector to the moveable joint, such as a universal joint, to the first end of the longitudinally extending shaft. The holder is designed to either hold a reaming or cutting tool or to hold an acetabular implant. Since the holder is coupled at a connection point to the moveable joint on the end of the longitudinal shaft, it can be oriented in any angular position or at least a wide range of desired positions with respect to the shaft. The shaft has a shaft bearing mounted on the shaft adjacent an end opposite the holder end. The bearing may be mounted in a fixed position along the length of the shaft. The shaft may be a drive shaft used to rotate within the shaft bearing and drive the reamer or other tool via the universal or flexible joint. The positioner has a longitudinally extending first arm pivotally connected to the shaft bearing at a first pivot point for pivotal movement in a plane parallel or coplanar to the shaft longitudinal axis. The first arm preferably includes a handle portion. The tool includes a second arm pivotally connected to the first arm at a second pivot point and pivotally connected to the holder at a third pivot point. The first arm of the positioning tool has a mounting rod on which the tracker is mounted. In a preferred embodiment, the tracker emitter array includes at least three light emitting diodes to enable the optical tracking system to calculate the position of the arm. The array mounting rod extending from the first arm preferably extends at a point thereon located outwardly of a handle portion on the first arm, which handle is used by the surgeon to manipulate the positioning tool to position the holder at the desired location. The axis of the tracker is oriented at a fixed angle to the holder central axis, and may be parallel thereto to allow the optical tracking system to locate the holder central axis based on tracker data. Mounting the mounting arm parallel to the central axis allows the surgeon to visualize the angle of the holder by the orientation of the tracker mounting rod.

Preferably, the shaft bearing is fixed axially along the longitudinally extending shaft and the first, second and third pivot points are located at distances from one another so as to position the central axis of the holder at an angle with respect to the first end of the longitudinal shaft in fixed relationship to the angle of the tracker mounting rod for all pivotal positions of the first arm with respect to the shaft bearing. This means that the central axis of the holder is located at a fixed angle or parallel to the axis of the tracker mounting rod as the positioning tool first arm is manipulated to any position with respect to the longitudinal shaft. As will be easily understood by one skilled in the art, the structure described is in the form of a four bar linkage with the lengths of the various arms and the locations of the pivot points on the arms connecting the adjacent sides of the linkage chosen to establish a known geometric relationship between the emitter (tracker) array and the reaming tool or implant mounted on the tool. In the preferred embodiment, the four arms form a parallelogram with opposite sides being the same length. Of course as long as the geometry of the tool is programmed into the computer, mathematical algorithms can calculate the position of the cutting head based on inputs of the optical tracking system.

The positioning tool is used by mounting the implant or instrument on the holder and mounting the tracker on the mounting rod attached to the first arm. The surgeon then can manipulate the positioner and the holder about the moveable joints to any desired position. An optical tracking system coupled to the computer-assisted surgical system can calculate the location of the implant or cutting tool from the known relationships of the linkage system and the known angle of the holder central axis which is at a fixed angle or is parallel to the central axis of the rod holding the light emitting diode tracker assembly. The holder, including cutting tool or implant, is placed within the patient and the optical tracking system allows the surgeon to view the joint, such as the acetabulum, on the CRT with the computer generated location of the cutting tool or implant overlayed either on the digital CT images stored in the computer database for the patient or on a vertical acetabulum. The movement (image free) of the holder is tracked in real time and the real or virtual image data is updated to compensate for patient movement, if any, also in real time. The surgeon can then manipulate the holder via the handle on the first arm to cut the proper cavity or locate the implant in its desired position. When used without the optical computer-aided system, the instrument can still be used utilizing the parallel relationship between the mounting rod on the handle and the holder central axis.

DETAILED DESCRIPTION

Referring to the figures, there is shown an acetabular cup or tool positioner of the present invention generally denoted as 10. Positioner 10 is essentially designed as a four bar linkage having a holder at its leading end design either to hold a cutting tool, such as an acetabular reamer or an implant such as a prosthetic acetabular cup. Of course the tool can be used to position other implants within the body.

Figure 1:
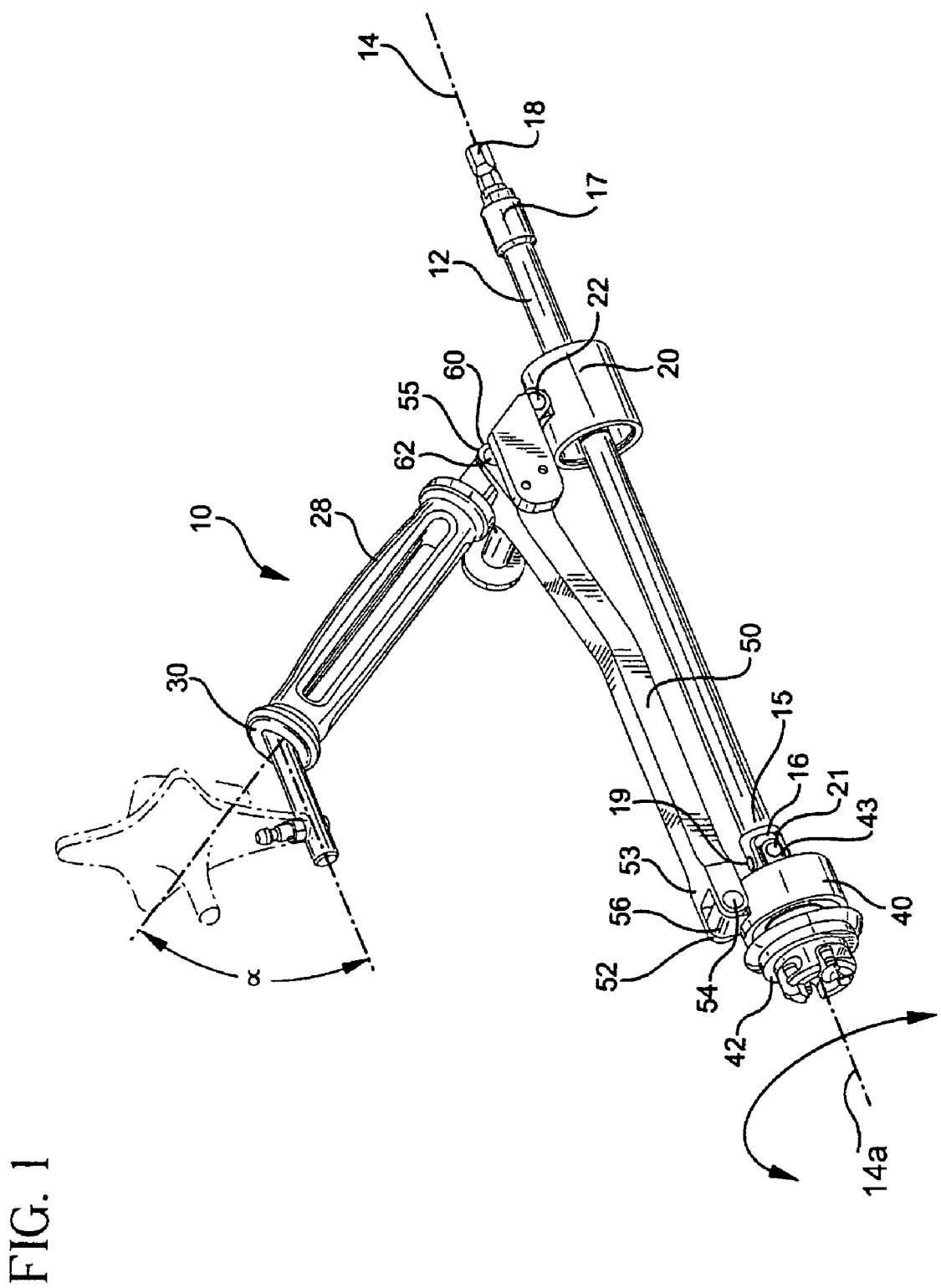
FIG. 1 is a side isometric view of the positioning tool of the present invention.
Figure 9:
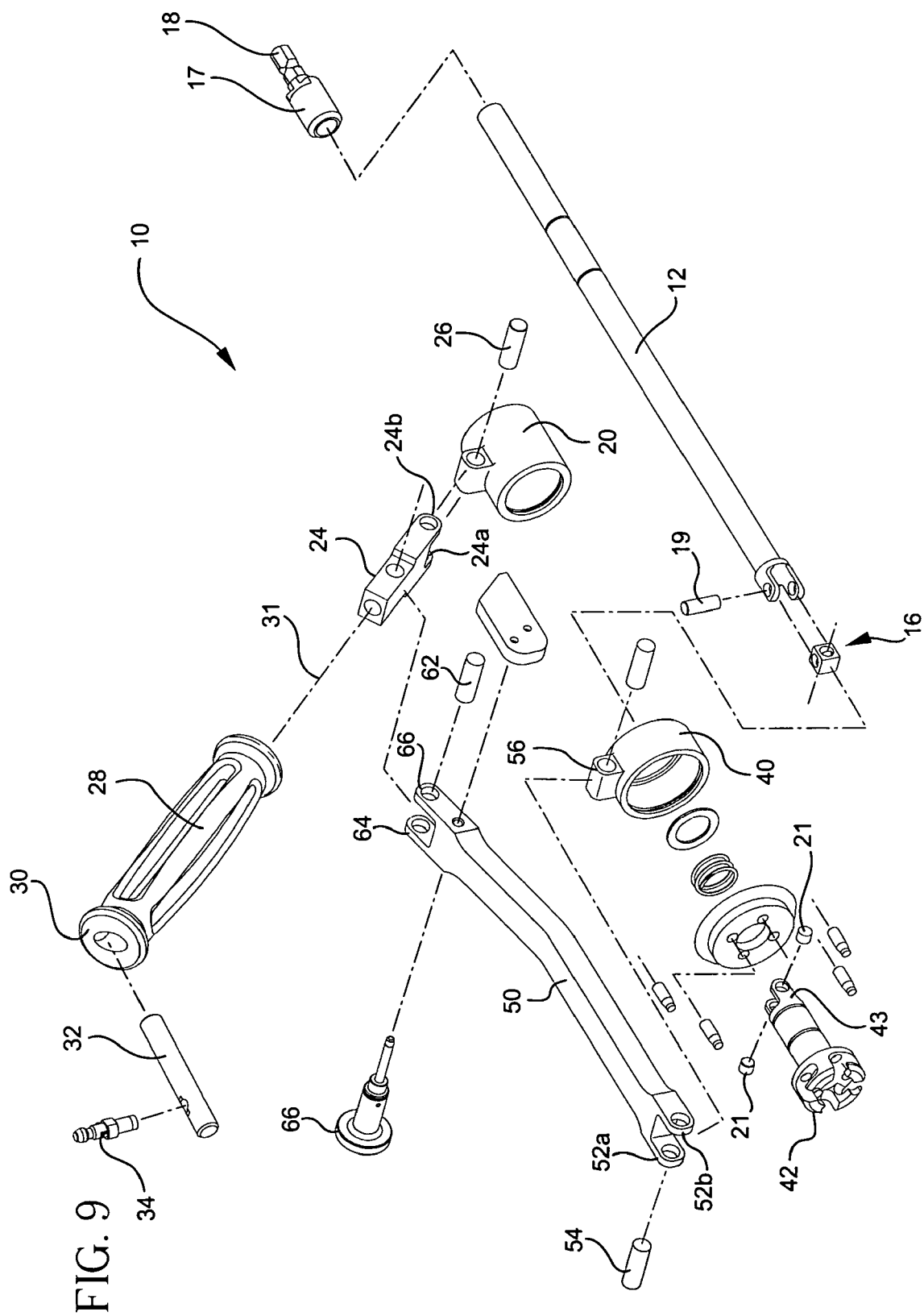
FIG. 9 is an exploded view of the positioning tool of FIG. 1.

Referring to FIGS. 1 and 9, there is shown a positioning tool 10 which includes a drive shaft 12 extending along a longitudinal axis 14. At a first end 15, drive shaft 12 includes a joint 16 capable of movement about at least two axis such as a flexible shaft or wire or a typical mechanical universal joint which is of a well known design and sized to fit the diameter of the shaft. At a second end 17 of shaft 12, there is a drive connection 18 adapted to engage a chuck (not shown) of any typical rotary power drive such as an electric drill. Shaft 12 has a bearing member 20 mounted thereon. Bearing 20 is fixed axially on shaft 12 but allows the shaft 12 to rotate about axis 14 of shaft 12. Bearing 20 includes a pivot connection 22 on an outer surface thereof.

As best seen in FIGS. 2–5 and 9, pivot connection 22 is pivotally connected to a first arm 24 via a pivot pin 26 and a pair of forks 24a and 24b. The preferred first arm 24 includes handle 28 coupled thereto which has a first end 30 opposite pivot point 22. In the preferred embodiment, a mounting rod 32 extends at a predetermined angle α with respect to the longitudinal axis 31 of arm 24 and handle 28. Mounting rod 32 includes a connector 34 for connecting an emitter or tracker array 36 to the first arm 24. In the preferred embodiment, tracker array 36 includes at least three light emitting diodes 38 located in the same plane which diodes can be tracked by an optical tracking system such as described in U.S. Pat. Nos. 6,021,343 and 6,434,415, the teachings of which are incorporated herein by reference.

While in the preferred embodiment, an optical tracking system is used any tracking system such as acoustic system can be used. In addition, while the preferred tracker includes radiation (light), emitting diodes a passive system using light reflectors could also be used.

Moveable joint 16 attached to first end 15 of shaft 12 is coupled to a holder 40 which includes a mounting system 42 on which a cutting tool, such as a reamer 44 is mounted. The preferred universal joint 16 has a pair of perpendicular pins 19 and 21 about which two parts of the joint can pivot in a standard manner. Holding system 42 can be any suitable system for gripping an acetabular cup implant or acetabular reamer. In the preferred embodiment, the holder is similar to that taught in U.S. Pat. No. 6,264,647. Preferably, the holder can releasably grip both a reaming tool and the prosthetic acetabular cup.

Holder 40 has a central axis 14a and is coupled via a connector 43 to pin 21 at one end of the universal joint 16 50 that axis 14a may, in the preferred embodiment, be oriented in any angular relationship to axis 14 of shaft 12. In order to effectuate angular movement of holder 40, holder 40 is coupled to a second arm 50 via a pivot connection 52 having forks 52a and 52b. Pivot connection 52 is similar to the pivot connection 22 and includes a pivot pin 54 extending through a bushing 56 having a flange integrally formed on the outer circumference of holder 40. Thus, second arm 50 has a first end 53 pivotally coupled to the holder 40 and a second end 55 pivotally connected to first arm 24 at pivot connection 60. In the preferred embodiment, the pivot connection 60 consists of a pivot pin 62 which extends through a pair of forks 64, 66 formed on second end 55 of second arm 50 and, in the preferred embodiment, through a portion of arm 24.

The resulting structure can be seen to be a four bar linkage where each of the four bars are pivotally connected. The linkage is thus made up of shaft 12, first arm 24, holder 40 and second arm 50. In the preferred embodiment, the distances between the pivot points connecting the four bars and the angle α are chosen such that the axis 32 of mounting rod 34 always remains parallel to axis 44 of holder 40 throughout any location of first arm 24 and consequently any position of the four bar linkage.

In the preferred embodiment, the linkage forms a parallelogram with the distance between the pivot connection of universal joint 16 and pivot point 22 on bearing 20 along shaft 12 is approximately 6.6 inches and the length of second arm 50 between points 52, 60 is also approximately 6.6 inches. In the preferred embodiment, the distance of pivot point 54 from the center line 14a of holder 40 is approximately 0.79 inches. Likewise, the distance between pivot point 22 of bearing 20 from the axis 14 of shaft 12 is also approximately 0.79 inches. In the preferred embodiment, the distance between pivot point 22 and pivot point 60 a first arm 24 and second arm 50 respectively is approximately 1 inch and the distance between pivot point 52 and pivot point 21 is also 1 inch. The axis of all the pivot pins (except pin 19) are parallel so that movement of handle 20 takes place in a plane containing axis 14 of shaft 12.

Figure 2:
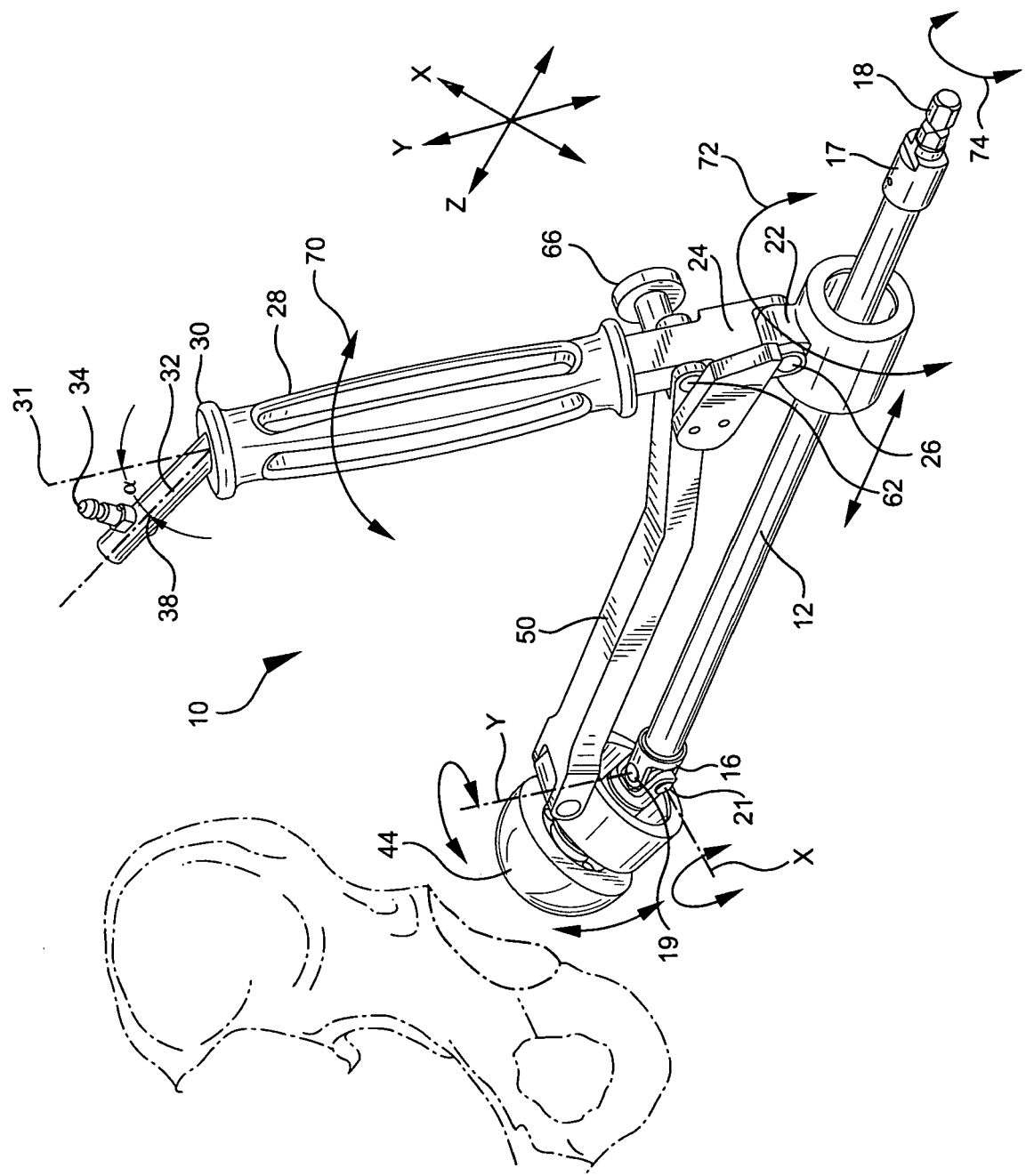
FIG. 2 is an isometric view of the positioning tool of the present invention, including an acetabular reamer position to shape the natural socket of the acetabulum.
Figure 3:
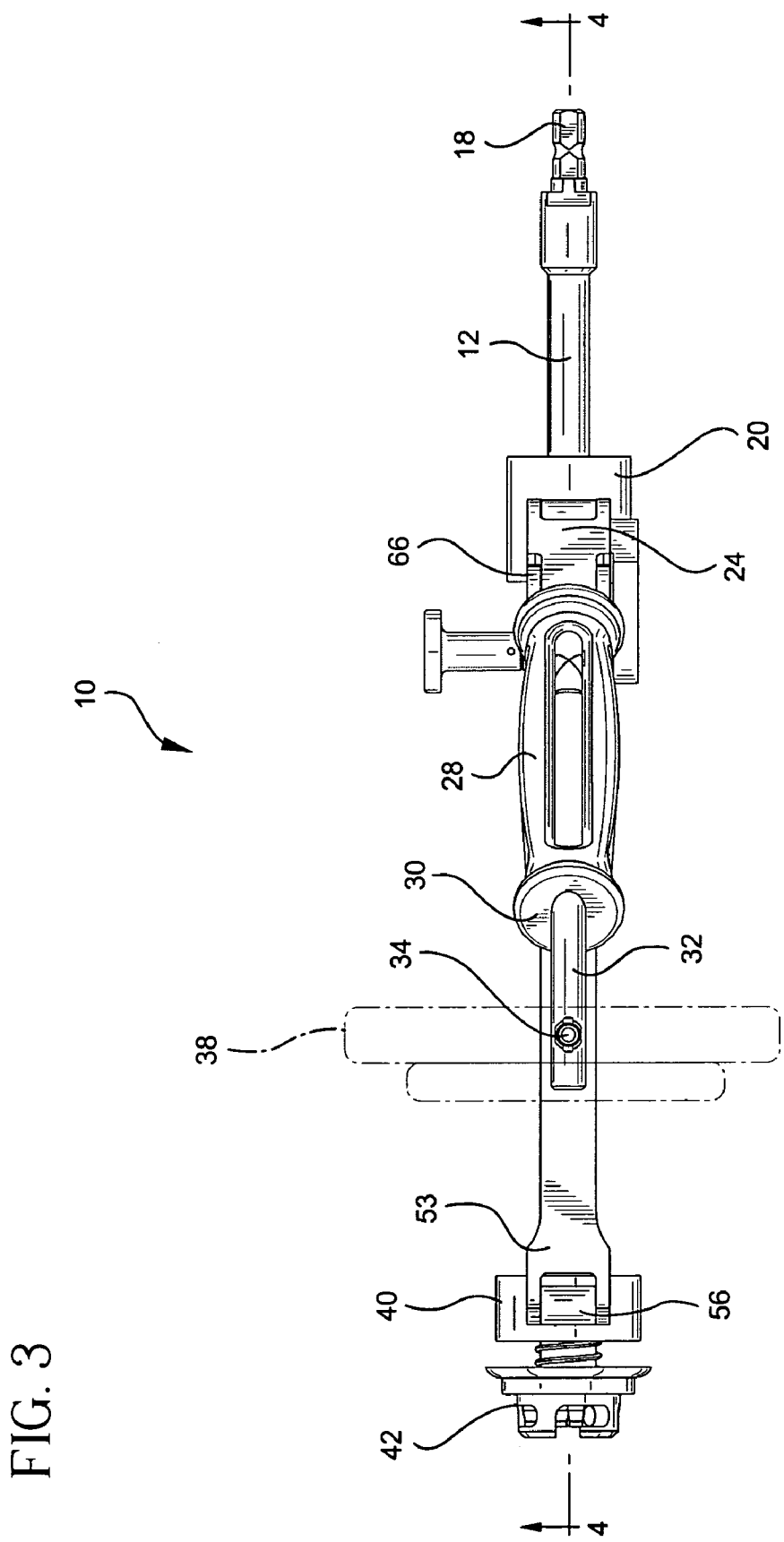
FIG. 3 is a top view of the positioning tool of the present invention shown in FIG. 1.
Figure 4:
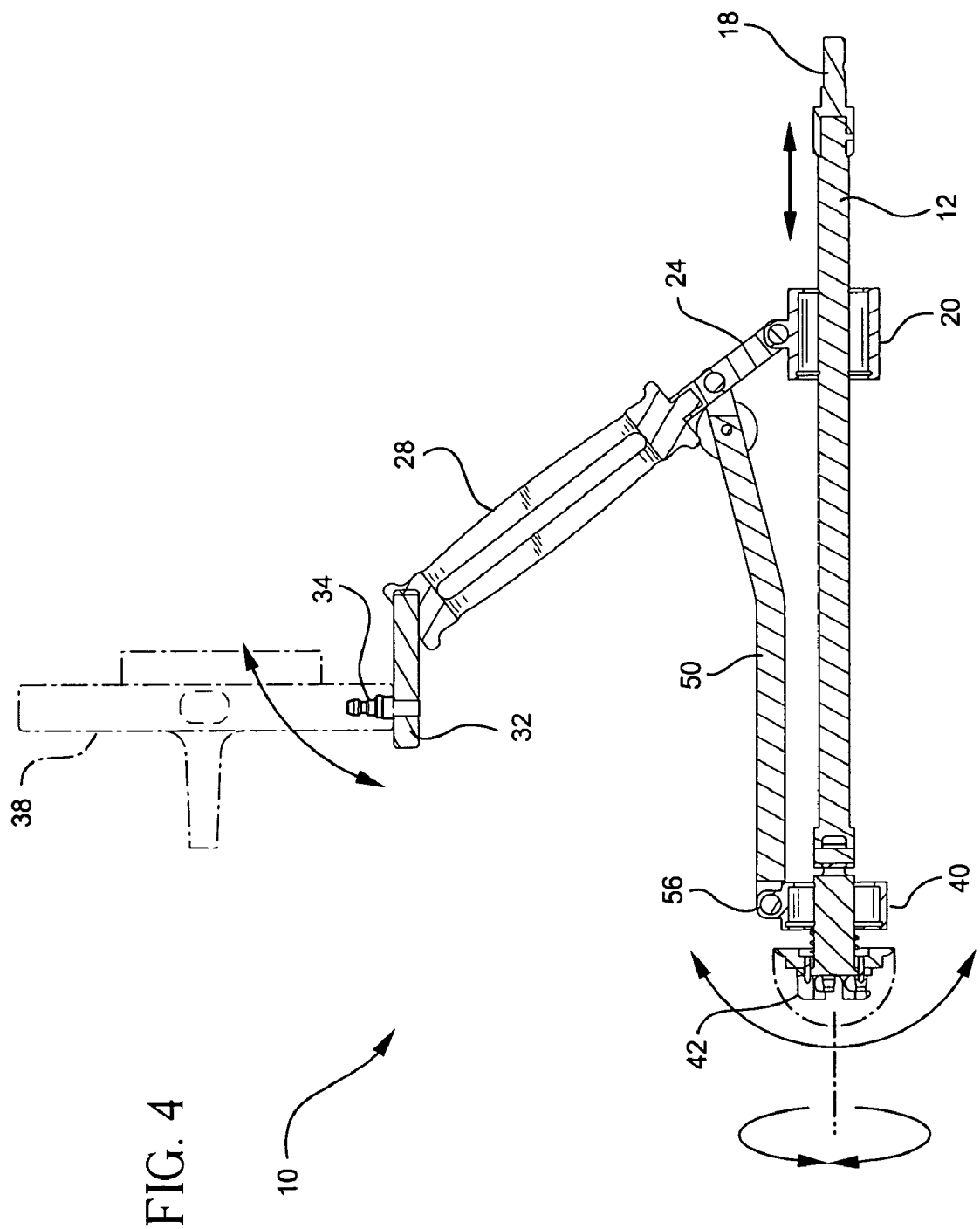
FIG. 4 is a cross-sectional view of the positioning tool of FIG. 3 along the lines 4—4.
Figure 5:
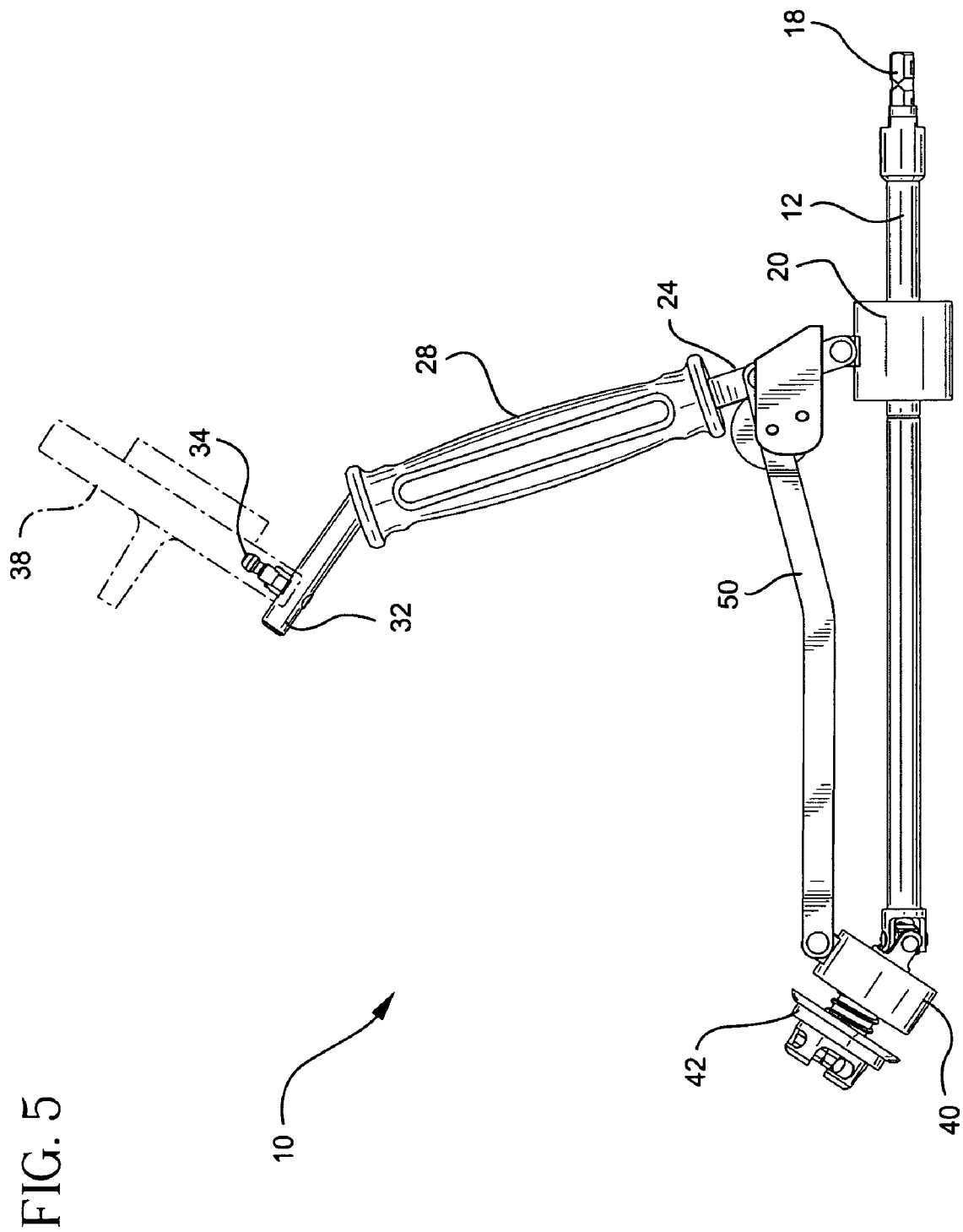
FIG. 5 is a side elevation view of the positioning tool of FIG. 1.
Figure 7:
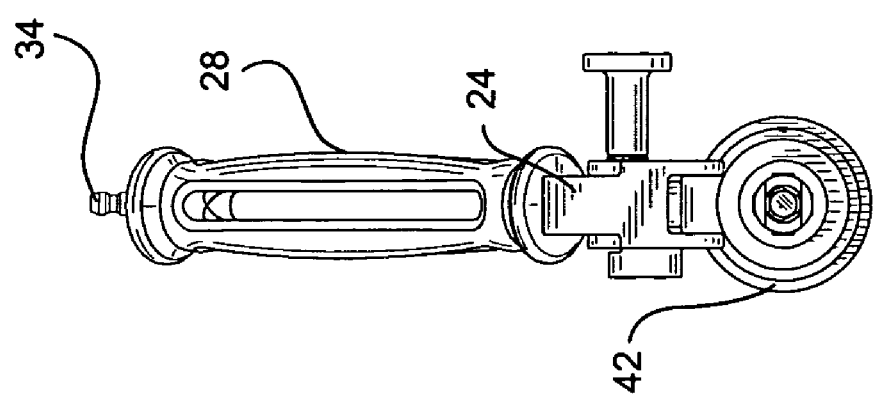
FIG. 7 is a rear end view of the positioning tool of FIG. 1.
Figure 6:
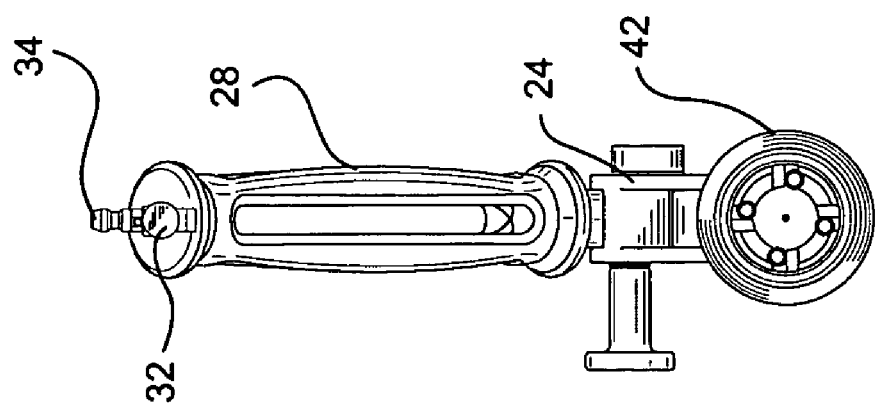
FIG. 6 is a front end view of the positioning tool of FIG. 1.
Figure 8:
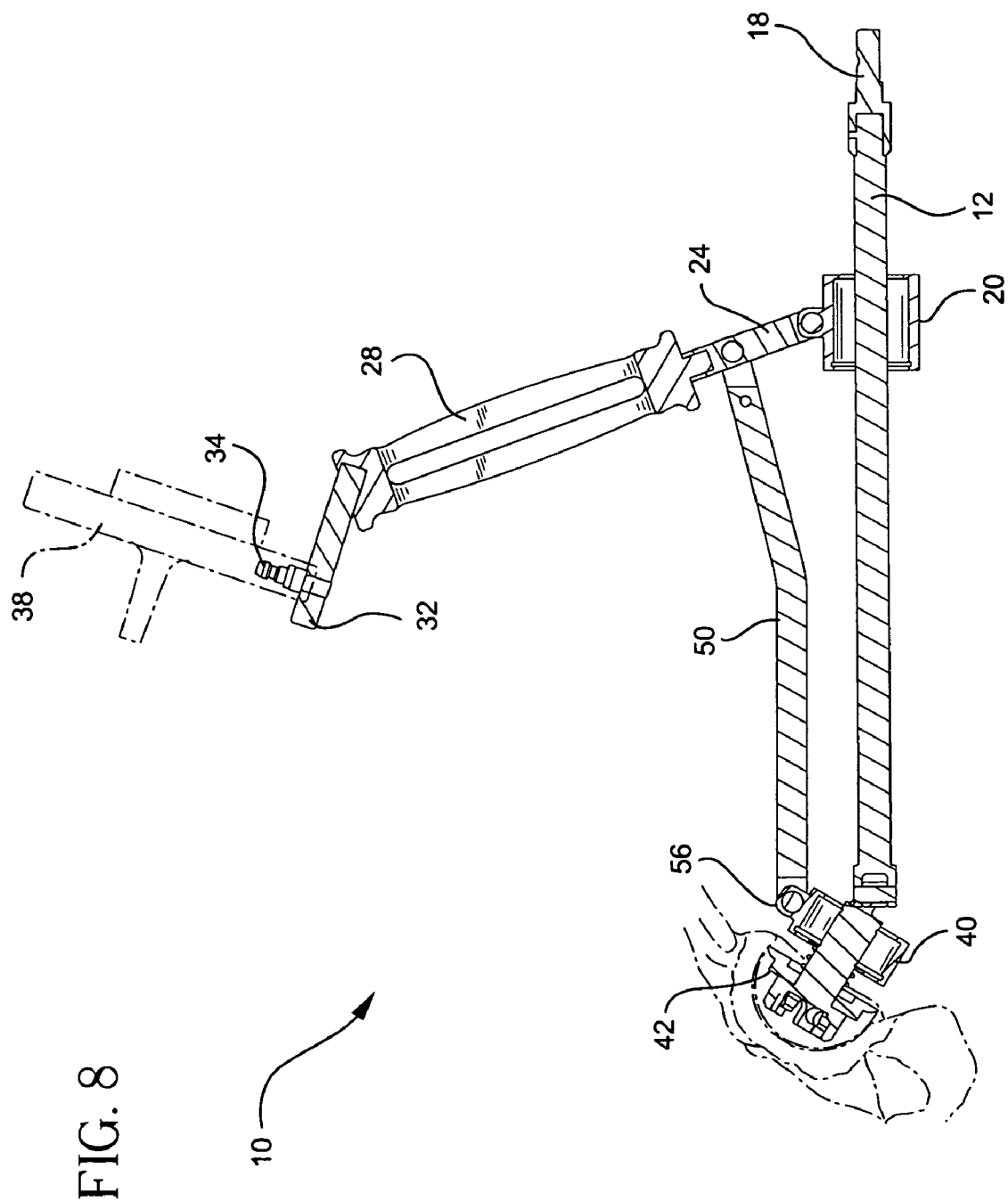
FIG. 8 is a cross-sectional view of the positioning tool of FIG. 3 along the lines 8—8.

During the preferred surgical procedure and after the optical-aid surgical system has been calibrated to the patient's anatomy, the instrument 10, including tracker assembly 36 mounted on rod 32 is grasped by the surgeon with one hand on handle 28. A cutting element or implant, such as a reamer or acetabular cup, denoted as 44 would be mounted on holder 40. In the case of reaming, a drive source, not shown, would be connected to drive element 18 on second end 17 of shaft 12 for powering the reamer. The positioner 10 is then inserted into an appropriate incision with the holder being aligned in the desired position via the computer-assisted surgical system. The surgeon may then manipulate handle 28 by manipulating the four bar linkage such as, for example, by rotating the handle along arrow 70 of FIG. 2. The surgeon may also rotate the entire assembly 10 about axis 14 of shaft 12 in the direction of arrow 72 of FIG. 2. The simultaneous movement of positioner 10 in direction 72 and the handle 28 and first arm 24 in direction 70 causes movement of cutting tool or acetabular cup 44 about the x, y and z axis of the universal joint 16. Such manipulation would be shown on the CRT with respect to either the stored actual images or virtual images of the patient joint by the tracking system. Upon obtaining the correct position adjacent the joint sockets, for example, the acetabulum, the drive shaft 12 and reamer is activated via drive element 18 with a suitable drive and rotating the shaft in a direction 74 about axis 14 (FIG. 2).

Once the reaming is complete, the instrument is removed from the patient and the reamer is replaced by the acetabular implant which is located in the desired orientation with the computer-aided tracking system. The cup is then implanted in a standard manner. If a tracker system is not used the surgeon can orient the reamer or implant via rod 32 since, in the preferred embodiment, it is parallel in all orientations to the holder central axis. If visual orientation is not needed, i.e., a computer-aided tracking system will always be used during surgery it may be possible to mount the tool geometry and tracker array in any orientation. The computer can then be programmed with the tracker orientation and calculate the correct holder orientation. Thus, the four-bar linkage need not be parallel as long as the actual geometry of the linkage were correctly programmed into the computer so that the actual holder orientation could be calculated based on the position of tracker 38.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A positioning tool for a cutting instrument or implant, comprising:
   a shaft having a longitudinal axis and a first pivot connection capable of angular movement at a first end;
   a holder having a central axis for holding the instrument or implant coupled to said first pivot connection for angular movement with respect to said shaft first end;
   a shaft bearing rotatably mounted on said shaft;
   a first arm pivotally connected to said shaft bearing at a second pivot point for pivotal movement in a plane parallel to said shaft axis; and
   a second arm pivotally connected to said first arm at a third pivot point and said holder at a fourth pivot point.

2. The positioning tool as set forth in claim 1, wherein said first pivot connection is a universal joint.

3. The positioning tool as set forth in claim 1, wherein said first arm has a tracking device thereon.

4. The positioning tool as set forth in claim 3, wherein said tracking device is selected from the group consisting of an active array, a passive array, a sonic array, a light emitting diode array light, a reflective array, an electromagnetic tracker and a laser emitting tracker.

5. The positioning tool as set forth in claim 3, wherein the first arm has a mounting element for mounting said tracker device thereon, said mounting element has an axis extending at a fixed angle to said central axis of said holder at any pivotal position of said first arm.

6. The positioning tool as set forth in claim 5, wherein the first pivot connection is positioned axially on said shaft and said second, third and fourth pivot points are positioned relative to each other to position the central axis of the holder with respect to said mounting element axis at said fixed angle.

7. The positioning tool as set forth in claim 6, wherein the distance between said first pivot connection at said shaft first end and said second pivot point equals the distance between said third and fourth pivot points.

8. The positioning tool as set forth in claim 7, wherein the distance between said first pivot connection on said first end of said shaft and fourth pivot point is equal to the distance between said second and third pivot points.

9. The positioning tool as set forth in claim 5, wherein said mounting element is a rod extending from said first arm along said mounting element axis.

10. The positioning tool as set forth in claim 9, wherein said holder central axis is parallel to said rod axis for all positions of said first arm with respect to said shaft.

11. The positioning tool as set forth in claim 1, wherein said first arm includes a handle.

12. The positioning tool as set forth in claim 1, wherein said shaft, said holder, said first arm and said second arm form a four bar linkage in the form of a parallelogram.

13. The positioning tool as set forth in claim 12, wherein the simultaneous movement of said positioning tool and pivoting of the first arm with respect to said shaft causes said holder to be oriented in any desired position with respect to a bony target.

14. The positioning tool as set forth in claim 13, wherein said first arm includes a mounting rod extending along an axis at a fixed angle to said first arm which angle maintains said mounting rod parallel to said holder central axis as said first arm pivots about said second pivot point.

15. The position tool as set forth in claim 14, wherein a tracker for an optical tracking system is mounted on said mounting rod.

16. The positioning tool as set forth in claim 15, wherein said tracker array is a light emitter diode array.

17. The positioning tool as set forth in claim 16, wherein said light emitting diodes are tracked by an optical tracking system which is able to locate the position of said holder with respect to said bony target from a tracked location of said array.

18. The positioning tool as set forth in claim 1, wherein said shaft is a drive shaft having a second end adapted to be coupled to a drive source.

19. The positioning tool as set forth in claim 1, wherein a range of angular movement of said holder with respect to said first shaft is at least to 90°.

20. A method for positioning an implant or instrument in the joint socket of a patient comprising:
mounting the implant or instrument on a holder of a positioning tool, the tool having a shaft with a moveable joint at a first end thereof connected to said holder at a first pivot point, a first arm pivotally connected to said shaft at a second pivot point, a second arm pivotally connected to said first arm at a third pivot point and said holder at a fourth pivot point;
placing the mounted implant or instrument adjacent the joint socket;
guiding the mounted implant or instrument with respect to the joint socket by moving said first arm with respect to said shaft about said second pivot point.

21. The method as set forth in claim 20 further including guiding the implant or instrument using at least in part, a tracking system mounted on said first arm.

22. The method as set forth in claim 20 wherein said guiding said implant or instrument is performed, at least in part, by an optical tracking system.

23. The method as set forth in claim 20, wherein said tracker is mounted on an axis which is in a fixed relationship to a central axis of the implant or instrument throughout the movement of said first arm.

24. The method as set forth in claim 23, wherein the tracker mounting axis and the central axis are parallel.

25. The method as set forth in claim 20, wherein said guiding of said implant or instrument further includes rotating said first and second arm around said shaft.

26. The method as set forth in claim 25, wherein said first arm includes a handle.

* * * * *

UNITED STATES PATENT AND TRADEMARK OFFICE
CERTIFICATE OF CORRECTION

PATENT NO. : 7,008,430 B2 Page 1 of 1
APPLICATION NO. : 10/356075
DATED : March 7, 2006
INVENTOR(S) : Nicholas Nai Guang Dong, Michael Nogler and Martin Krismer It is certified that error appears in the above-identified patent and that said Letters Patent is hereby corrected as shown below:

On Title Page (item 57)
    ABSTRACT, line 1, "instrument or a" should read --instrument or an--.
    ABSTRACT, line 8, "such a drill" should read --such as a drill--.
    Column 2, line 42, after "instrument", insert --may be--.
    Column 3, line 46, after "Of course", insert --,--.
    Column 4, line 38, after "reamer", insert --,--.
    Column 4, line 39, after "Of course", insert --,--.
    Column 5, line 4, "(light), emitting diodes" should read --(light) emitting diodes.--.
    Column 5, line 8, "44 is mounted" should read --44, is mounted--.
    Column 5, line 46, "is" should read --being--.
    Column 5, line 56, "axis" should read --axes--.
    Column 5, line 62, after "32", insert --,--.
    Column 5, line 64, after "44", insert --,--.
    Column 6, line 16, "is" should read --are--.
    Column 6, line 17, "rotating" should read --rotates--.
    Column 6, line 28, "surgery it" should read --surgery, it--.
    Column 6, line 33, "were" should read --was--.
    Column 8, line 27, after "using", insert --,--.

Signed and Sealed this

Twenty-second Day of August, 2006

JON W. DUDAS
*Director of the United States Patent and Trademark Office*